United States Patent [19]

Lee et al.

[11] Patent Number: 5,160,414
[45] Date of Patent: Nov. 3, 1992

[54] EXTRACTIVE DISTILLATION OF ALCOHOL/ETHER/HYDROCARBON MIXTURES

[75] Inventors: Fu-Ming Lee; Robert L. Hair; Ronald E. Brown, all of Bartlesville, Okla.

[73] Assignee: Phillips Petroleum Company, Bartlesville, Okla.

[21] Appl. No.: 732,981

[22] Filed: Jul. 19, 1991

[51] Int. Cl.⁵ .................. B01D 3/40; C07C 41/42
[52] U.S. Cl. .................................. 203/57; 203/58; 203/64; 203/74; 203/80; 203/81; 568/699; 585/857; 585/860; 585/865
[58] Field of Search .............. 203/57, 74, 58, 64, 203/80, 81; 585/833, 857, 860, 865; 568/697, 699, 708

[56] References Cited

U.S. PATENT DOCUMENTS

| | | | |
|---|---|---|---|
| 3,366,568 | 1/1968 | Eisenlohr et al. | 208/313 |
| 3,415,742 | 12/1968 | Eisenlohr et al. | 208/323 |
| 4,012,289 | 3/1977 | Haskell | 203/51 |
| 4,053,369 | 10/1977 | Cines | 203/52 |
| 4,121,978 | 10/1978 | Becuwe | 203/58 |
| 4,148,695 | 4/1979 | Lee et al. | 203/63 |
| 4,401,517 | 8/1983 | Lee | 203/53 |
| 4,459,178 | 7/1984 | Berg et al. | 203/51 |
| 4,513,153 | 4/1985 | Sandrin | 568/697 |
| 4,661,209 | 4/1987 | Berg | 203/51 |
| 4,676,874 | 6/1987 | Berg et al. | 203/51 |
| 4,735,690 | 4/1988 | Berg et al. | 203/51 |
| 4,921,581 | 5/1990 | Lee et al. | 203/56 |
| 4,944,849 | 7/1990 | Lee | 203/55 |
| 4,948,470 | 8/1990 | Lee | 203/51 |
| 4,948,472 | 8/1990 | Lee et al. | 203/55 |
| 4,954,224 | 9/1990 | Brown et al. | 203/51 |
| 4,955,468 | 9/1990 | Lee | 203/53 |
| 5,032,232 | 7/1991 | Lee et al. | 203/51 |

FOREIGN PATENT DOCUMENTS 0047204 3/1982 European Pat. Off. ............ 203/57

Primary Examiner—Virginia Manoharan
Attorney, Agent, or Firm—K. K. Brandes

[57] ABSTRACT

An extractive distillation process for separation ethers (in particular methyl t-butyl ether or ethyl t-butyl ether), aliphatic hydrocarbons (in particular isobutane and/or isobutene) and alcohols (in particular methanol or ethanol) employs as solvent sulfolane(s) and/or dialkyl sulfone(s), or N-(β-mercaptoalkyl)-2-pyrrolidone(s), or a mixture of N-alkyl-2-pyrrolidone(s) and either sulfolane(s) or glycol compound(s).

49 Claims, 1 Drawing Sheet

EXTRACTIVE DISTILLATION OF ALCOHOL/ETHER/HYDROCARBON MIXTURES

BACKGROUND OF THE INVENTION

In one aspect, this invention relates to the separation of ethers and aliphatic hydrocarbons from alcohols by extractive distillation. In another aspect, this invention relates to the recovery of ethers from a mixture containing ether(s), alcohol(s) and aliphatic hydrocarbon(s).

Extractive distillation is a well known technique for separating mixtures of components which exhibit relative volatilities close to unity (i.e., having nearly equal volatility and having nearly the same boiling point) and/or which form azeotropes (such as mixtures of ethyl-t-butylether and ethanol). It is difficult to separate the components of such mixtures by conventional fractional distillation. In extractive distillation, a solvent is introduced into a distillation column above the entry point of the feed mixture which is to be separated. The solvent affects the relative volatility of the feed components and/or attractive forces between components of azeotropes sufficiently to facilitate the separation of the various feed components by distillation, as has been described in the article entitled "Extractive Distillation Saves Energy" by Ian Sucksmith, Chemical Engineering, Jun. 28, 1982, pages 91-95. Other literature sources on extractive distillation techniques include "Handbook of Separation Techniques for Chemical Engineers" by Philip A. Schweitzer, McGraw-Hill Book Company, 1979, pages 1-135 to 1-143; and Perry's Chemical Engineers Handbook, 6th Edition, McGraw-Hill Book Company 1984, pages 13-53 to 13-57.

SUMMARY OF THE INVENTION

It is an object of this invention to provide a process for separating ethers and aliphatic hydrocarbons from alcohols by extractive distillation employing a selective solvent (also referred to as extractant or entrainer). It is another object of this invention to provide a process for recovering ether(s) from a mixture containing ether(s), alcohol(s) and aliphatic hydrocarbons(s). Other objects and advantages will be apparent from the detailed description of the invention and the appended claims.

In accordance with this invention, a process for separating ethers, aliphatic hydrocarbons and alcohols comprises the step of extractive distillation of a feed comprising (a) at least one ether containing 4 to 8 carbon atoms per molecule, (b) at least one aliphatic hydrocarbon selected from the group consisting of alkanes containing 3 to 7 carbons atoms per molecule and alkenes containing 3 to 7 carbon atoms per molecule, and (c) at least one saturated aliphatic alcohol containing 1 to 5 carbon atoms and one OH group per molecule, said process employing at least one solvent selected from the group consisting of:

(A) sulfolane compounds, (as defined by Formula 1 in Column 5 of U.S. Pat. No. 4,053,369,) containing 4-8 carbon atoms per molecule and having the general formula of

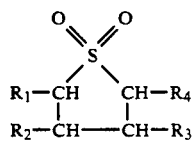

wherein $R_1$, $R_2$, $R_3$, and $R_4$ are independently selected from the group comprising hydrogen and methyl. wherein said extractive distillation produces (i) an overhead distillate product which contains a larger volume percentage of said at least one ether than said feed, a larger volume percentage of said at least one aliphatic hydrocarbon than said feed and a smaller volume percentage of said at least one alcohol than said feed, and (ii) a bottoms product which contains said at least one solvent, a smaller percentage of said at least one ether than said feed, a smaller percentage of said at least one hydrocarbon than said feed, and a larger percentage of said at least one alcohol than said feed.

Also in accordance with this invention, a process for separating ethers, aliphatic hydrocarbons and alcohols comprises the step of extractive distillation of a feed comprising (a) at least one ether containing 4-8 carbon atoms per molecule, (b) at least one aliphatic hydrocarbon selected from the group consisting of alkanes containing 3-7 carbon atoms per molecule and alkenes containing 3-7 carbon atoms per molecule, and (c) at least one saturated aliphatic alcohol containing 1 to 5 carbon atoms and one OH group per molecule, said process employing at least one solvent selected from the group consisting of:

(I) mixtures of at least one sulfolane compound, as defined above, and at least one dialkyl sulfone, as defined above;

(II) mixtures of at least one N-alkyl-2-pyrrolidone wherein the alkyl group contains 1-3 carbon atoms and at least one sulfolane compound, as defined above; and (III) mixtures of at least one N-alkyl-2-pyrrolidone and at least one glycol compound having the general chemical formula of HO—[CHR$^1$—CHR$^2$—O]$_n$—CHR$^1$CHR$^2$—OH, wherein n can be 0, 1, 2, 3, or 4, and R$^1$ and R$^2$ can be independently selected from the group consisting of hydrogen and methyl;

wherein said extractive distillation produces (i) an overhead distillate product which contains a larger volume percentage of said at least one ether than said feed, a larger volume percentage of said at least one aliphatic hydrocarbon than said feed and a smaller volume percentage of said at least one alcohol than said feed, and (ii) a bottoms product which contains said at least one solvent, a smaller percentage of said at least one ether than said feed, a smaller percentage of said at least one hydrocarbon than said feed, and a larger percentage of said at least one alcohol than said feed.

DETAILED DESCRIPTION OF THE INVENTION

Figure 1:
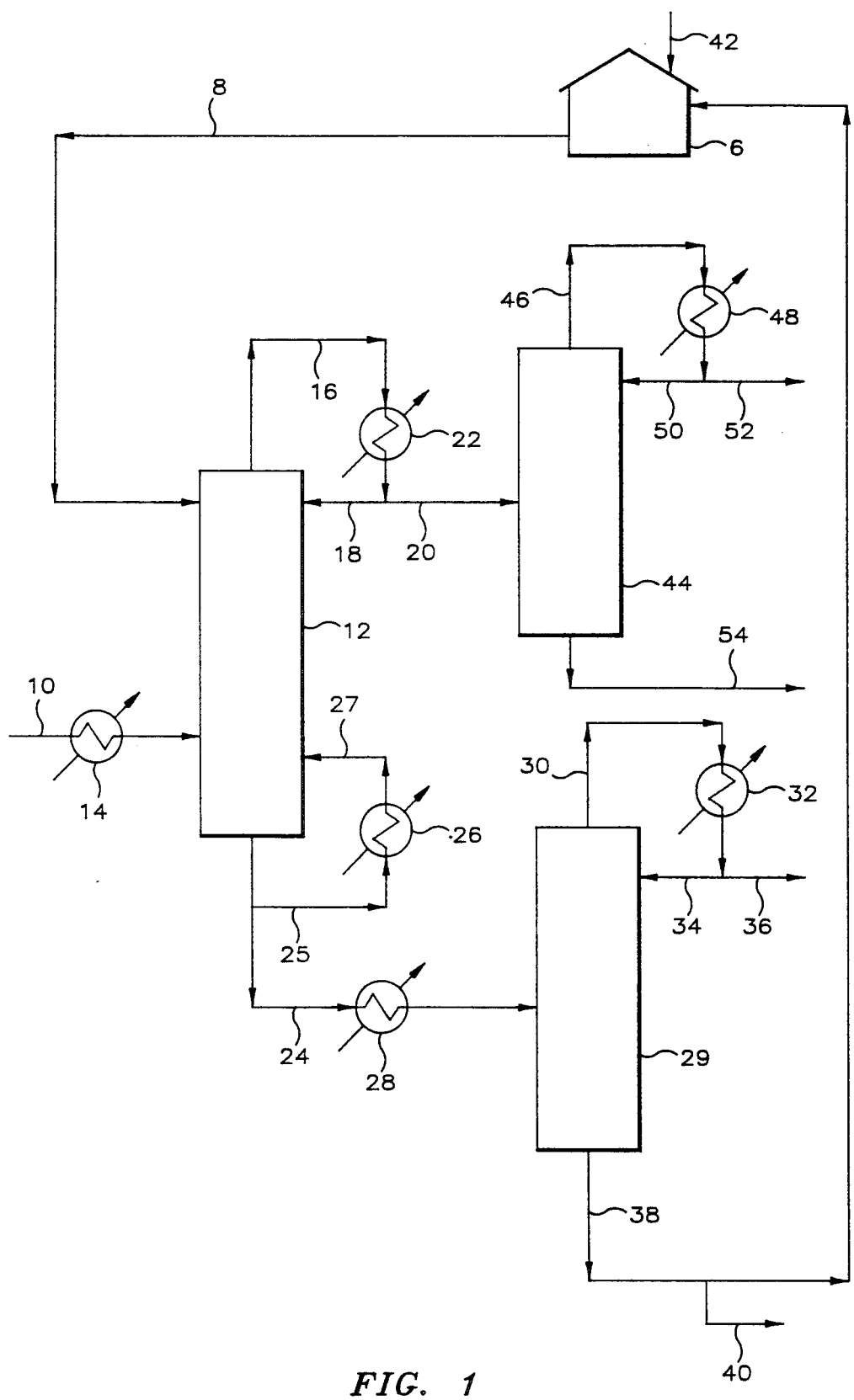
FIG. 1 illustrates the extractive distillation process of this invention.

In an extractive distillation process, a "solvent" (also called "extractant" or "entrainer") is added to a feed mixture of components in order to affect an effective separation of the components by distillation. The added solvent is usually chosen so as to exhibit high "selectivity" regarding the components to be separated. Selectivity is a term related to the change in volatilities of components in the mixture caused by the presence of the solvent. The larger the difference in relative volatility of the components in the mixture, the easier the separation of the components by fractional distillation becomes. Therefore, a solvent of high selectivity is a solvent which causes great differences between the relative volatilities of the components in a mixture, and will allow for the separation of components in a mixture with fewer distillation stages, lower amount of reflux and higher product purity.

In the processes of this invention, any feed which contains (preferably consists essentially of) at least one $C_4$-$C_8$ ether, at least one $C_3$-$C_7$ aliphatic hydrocarbon (preferably alkane) and at least one $C_1$-$C_5$ monohydric alcohol can be employed. Any suitable weight ratio of ether(s) to hydrocarbon(s) and alcohol(s) can be employed. Preferred ether:hydrocarbon weight ratios are in the range of about 0.2:1 to about 4:1 (more preferably about 0.4:1 to about 2:1). Preferred ether:alcohol weight ratios are in the range of about 4:1 to about 30:1 (more preferably about 6:1 to about 25:1). Generally, the boiling point of the feed mixture is in the range of about 10° to about 250° F., at a pressure of about 0 psig.

Non-limiting examples of suitable feed ethers are: methyl tertiary-butyl ether, ethyl tertiary-butyl ether, methyl tertiary-pentyl ethyl, ethyl tertiary-pentyl ether, and methyl tertiary-hexyl ether; preferably methyl tertiary-butyl ether or ethyl tertiary-butyl ether.

Non-limiting examples of suitable feed alkanes are propane, n-butane, isobutane, n-pentane, 2-methylbutane, n-hexane, 2-methylpentane, 3-methylpentane, and mixtures thereof; preferably isobutane.

Non-limiting examples of suitable feed alkenes are propylene, 1-butene, 2-butene, 2-methylpropene (isobutene), 1-pentene, 2-pentene, 2-methyl-1-butene, 1-hexene, 2-hexene, 3-hexene, 2-methyl-1-pentene, 2-methyl-2-pentene, 3-methyl-1-pentene, 2,3-dimethyl-1-butene, and mixtures thereof; preferably isobutene.

Non-limiting examples of feed alcohols which are methanol, ethanol, 1-propanol, 2-propanol, 1-butanol, 2-butanol, 2-methyl-1-propanol, tertiary butanol, 1-pentanol, 2-pentanol, 2-methyl-1-butanol, 2-methyl-2-butanol and mixtures thereof; preferably methanol or ethanol.

Non-limiting examples of sulfolanes which are suitable as solvent, either alone or in admixture with dialkylsulfone(s) are: unsubstituted sulfolane (cyclotetramethylene sulfone; also referred to as 2,3,4,5-tetrahydrothiophene-1,1-dioxide), 2-methylsulfolane, 3-methylsulfolane, 2,3-dimethylsulfolane, 2,4-dimethylsulfolane, 2-ethylsulfolane, 2,3,4,5-tetramethylsulfolane, and the like, and mixtures thereof. Presently preferred is unsubstituted sulfolane (cyclotetramethylene sulfone).

Non-limiting examples of dialkyl sulfones which are suitable as solvent, either alone or in admixture with sulfolane(s) are dimethyl sulfone, methyl ethyl sulfone, diethyl sulfone, ethyl n-propyl sulfone, di(n-propyl) sulfone, diisopropyl sulfone, ethyl n-butyl sulfone, n-propyl n-butyl sulfone, di(n-butyl) sulfone, diisobutyl sulfone, ethyl n-pentyl sulfone, n-propyl n-pentyl sulfone, n-butyl n-pentyl sulfone, di(n-pentyl) sulfone, and mixtures thereof; preferably di(n-propyl) sulfone.

Non-limiting examples of N-mercaptoalkyl-2-pyrrolidones are N-methylmercapto-2-pyrrolidone, N-($\beta$-mercaptoethyl)-2-pyrrolidone, N-($\beta$-mercaptopropyl)-2-pyrrolidone, N-($\gamma$-mercaptopropyl)-2-pyrrolidone, N-($\beta$-mercaptobutyl)-2-pyrrolidone, and mixtures thereof; preferably N-($\beta$-mercaptoethyl)-2-pyrrolidone, which can be prepared in accordance with the procedure described in U.S. Pat. No. 4,954,224.

Non-limiting examples of N-alkyl-2-pyrrolidones, which are useful as components of mixed solvents (admixed with sulfolane or glycol compounds) are N-methyl-2-pyrrolidone (preferred), N-ethyl-2-pyrrolidone and N-propyl-2-pyrrolidone, and mixtures thereof.

Non-limiting examples of glycol compounds which are suitable as a solvent component are: ethylene glycol, diethylene glycol, triethylene glycol, tetraethylene glycol and pentaethylene glycol, and mixtures thereof. Presently preferred is tetraethylene glycol.

Any suitable weight ratio of components in mixed solvents (I), (II) or (III) can be employed in the extractive distillation process of this invention. Preferably, the weight ratio of the first solvent component, e.g., sulfolane component(s) or N-alkyl-2-pyrrolidone(s), to the second solvent component, e.g., dialkyl sulfone(s) or glycol compound(s) is in the range of from about 0.05:1 to about 20:1, more preferably from about 0.2:1 to about 5:1.

Any suitable weight ratio of the solvent to the ether/hydrocarbon/alcohol containing feed mixture can be employed. Generally, the solvent to feed weight ratio is in the range of from about 1:1 to about 40:1, preferably in the range of from about 3:1 to about 20:1.

Any suitable reflux ratio (i.e., the weight ratio of the portion of condensed vapor which is returned to the distillation column to the portion of condensed vapor which is withdrawn as distillate product) can be employed in the extractive distillation process of this invention. Generally the reflux ratio is in the range of from about 0.1:1 to about 100:1, preferably in the range of from about 0.5:1 to about 50:1, more preferably in the range of from about 1:1 to about 20:1.

Any suitable feed entry location can be selected. Generally the feed entry location is in the range of from about 2 to about 70 percent of the total height of the packed or trayed column, measured upward from the bottom of the column, preferably in the range of from about 5 to about 60 percent, more preferably in the range of from about 7 to about 70 percent.

Any suitable solvent entry location can be selected. Generally the solvent entry location is in the range of from about 50 to about 99 percent of the total height of the packed or trayed column (i.e., within the upper half of the column), preferably in the range of from about 70 to about 99 percent, more preferably in the range of from about 80 to about 99 percent.

Any suitable temperature in the reboiler vessel (containing primarily the higher boiling feed components and the solvent) can be employed. The temperature is generally in the range of from about 100° to about 400° F., preferably in the range of from about 150° to about 320° F. The extractive distillation column is generally heated (more near the bottom, and less near the top). Generally, the temperature at the top of the column where the vapor exits into the condenser is in the range of from about 80° to about 300° F., preferably in the range of from about 100° to about 200° F. Solvent and feed are generally preheated (generally to a temperature close to the column temperature of the corresponding entry point) before they are introduced into the column. Any suitable pressure can be employed during the extractive distillation. Generally the pressure is about 5 to about 150 psig, preferably about 30 to about 100 psig.

Any suitable total column height, packed column height, column diameter and number of trays in the extraction distillation column can be employed. The exact dimensions and column designs depend on the scale of the operation, the exact feed composition, the exact solvent composition, the desired recovery and degree of purity of the various product, and the like, and can be determined by those having ordinary skills in the art.

The invention can be better understood by reference to FIG. 1 and the following description of a preferred embodiment of the invention. The feed mixture comprising ether(s), aliphatic hydrocarbon(s) and alcohol(s) is introduced through conduit 10 to a fractionation zone such as multi-stage distillation column 12. The temperature of the feed mixture flowing through conduit 10 can be adjusted as needed by controlling heat exchanger 14 so as to add heat to or remove heat from the feed mixture. Solvent from solvent storage 6 is introduced to distillation column 12 through conduit 8, and an overhead stream enriched in ether(s) and aliphatic hydrocarbon(s) is withdrawn from an upper portion of distillation column 12 through conduit 16.

The overhead stream passing through conduit 16 is condensed in condenser 22 to yield a condensed overhead stream. A portion of the condensed overhead stream is returned to distillation column 12 as reflux through conduit 18, while the remainder of the condensed overhead stream is passed through conduit 20 to distillation column 44. The distillation operation in column 44 yields overhead stream 46 which contains essentially all of the aliphatic hydrocarbon(s) and a bottoms stream 54 which contains essentially a pure ether product. Overhead stream 46 is at least partially condensed in condenser 48. A portion of the condensed overhead stream is returned as reflux stream 50 to column 44, whereas the remainder of the overhead stream is withdrawn as a substantially pure hydrocarbon stream 52.

A bottoms stream is withdrawn from a lower portion of the fractionation zone represented by distillation column 12 through conduit 24. A portion of the fluids withdrawn from the bottom of distillation column 12 may be heated and returned to distillation column 12. For example, a portion of the bottoms product stream can be withdrawn through conduit 25, heated in reboiler 26 and then passed back to a lower portion of distillation column 12 through conduit 27.

Operating conditions in heat exchanger 14, condenser 22 and reboiler 26 can be controlled and interfaced with solvent flow through conduit 8, feed mixture flow through conduit 10, reflux flow through conduit 18 and bottoms stream flow through conduit 24 such that the feed mixture introduced into distillation column 12 will be fractionated to yield an overhead stream which is enriched in ether(s) and aliphatic hydrocarbon(s) and a bottoms stream predominantly comprising the alcohol(s) and the solvent.

The bottoms stream passing through conduit 24 can be passed to storage, used in other processes or, preferably, passed to another fractionation zone, such as distillation column 29. Any adjustments to the temperature of the bottoms stream passing through conduit 24 necessary for efficient fractionation in distillation column 29 can be made by appropriately adjusting heat exchanger 28. An overhead stream predominantly comprising alcohol(s) is withdrawn from an upper portion of distillation column 29 through conduit 30. This overhead stream can be at least partially condensed in condenser 32. A portion of the overhead stream withdrawn from condenser 32 can be returned through conduit 34 as reflux for distillation column 29, with the remainder of the overhead alcohol stream being withdrawn as through conduit 36.

A bottoms stream predominantly comprising the solvent is withdrawn from a lower portion of distillation column 29 through conduit 38. A portion of this bottoms stream is preferably routed back to solvent storage 6 and then recycled to distillation column 12, while another portion of the bottoms stream is heated in a reboiler (not shown) and returned to the lower portion of column 29. From time to time, impurities which may build up in the solvent can be removed from the system by removing a small purge stream through conduit 40. Solvent lost through the purge stream or through other processing losses may be made up by a makeup stream passing through conduit 42 and into solvent storage 6.

The following examples are presented to further illustrate the invention and are not to be considered unduly limiting the scope of this invention.

EXAMPLE I

This example demonstrates the operability of unsubstituted sulfolane (cyclotetramethylene sulfone, hereinafter referred to as sulfolane), alone or in admixture with a dialkyl sulfone, in the extractive distillation of an ether/hydrocarbon/alcohol feed.

To a feed mixture comprising about 55 weight-% ethyl tert-butyl ether (ETBE), about 35 weight-% isobutane and about 6 weight-% ethanol was added an extractive solvent, either sulfolane alone or a mixture of 50 weight-% sulfolane and 50 weight-% di(n-propyl) sulfone (DPS), at various solvent: feed weight ratios. The total mixture (including the extractive solvent) was heated in a constant temperature bath to about 200° F., and the vapor was circulated in a Jurgensen equilibrium cell for about 20–30 minutes until a constant equilibrium pressure was attained. Then a small sample was withdrawn by means of a sample bomb from the flask containing the liquid phase of the equilibrium system, and a sample of the vapor was withdrawn by means of a sample bomb located just above the Jergensen cell. Both samples were analyzed, and the mole fractions of the three feed components in the liquid phase and in the vapor phase were determined by means of a gas chromatograph. The relative volatilities $R^1$ and $R^2$ were calculated as follows:

$$R^1 = \frac{Y1/Y2}{X1/X2} = \frac{Y1/X1}{Y2/X2}, \quad R^2 = \frac{Y3/Y2}{X3/X2} = \frac{Y3/X3}{Y2/X2}$$

wherein Y1 is the mole fractions of isobutane in the vapor phase, Y2 is the mole fraction of ethanol in the vapor phase, Y3 is the mole fraction of ETBE in the vapor phase, X1 is the mole fraction of isobutane in the liquid phase, X2 is the mole fraction of ethanol in the liquid phase, and X 3 is the mole fraction of ETBE in the liquid phase. Test results are summarized in Table I.

TABLE I

| Solvent:Feed Weight Ratio | Added Solvent | Relative Volatility $R^1$ | Relative Volatility $R^2$ |
|---|---|---|---|
| 0 | None | 14.6 | 0.4 |
| 1:1 | Sulfolane | 22.0 | 1.3 |
| 3:1 | Sulfolane | 22.7 | 1.7 |
| 3:1 | Sulfolane + DPS | 26.8 | 2.0 |
| 5:1 | Sulfolane | 35.6 | 4.9 |

TABLE I-continued

| Solvent:Feed Weight Ratio | Added Solvent | Relative Volatility $R^1$ | Relative Volatility $R^2$ |
| --- | --- | --- | --- |
| 5:1 | Sulfolane + DPS | 58.1 | 3.3 |

Based on the test results in Table I, it is concluded that sulfolane, dipropyl sulfone and mixtures thereof will be quite effective as solvents in the extractive distillation of feeds containing ether(s), aliphatic hydrocarbon(s) and alcohol(s), in particular at a solvent: feed weight ratio of about 5:1 or higher.

EXAMPLE II

This example demonstrates the superiority as solvent of a N-(β-mercaptoethyl)-2-pyrrolidone (MEP) versus N-methyl-2-pyrrolidone (NMP) in the extractive distillation of an ether/hydrocarbon/alcohol feed.

Tests were carried out substantially in accordance with the procedure described in Example I, except that MEP and NMP, respectively, was used as solvent. Test results are summarized in Table II. The feed mixture had the same composition as the one used in Example I.

TABLE II

| Solvent:Feed Weight Ratio | Added Solvent | Relative Volatility $R^1$ | Relative Volatility $R^2$ |
| --- | --- | --- | --- |
| 0 | None | 14.6 | 0.4 |
| 1:1 | MEP | 45.5 | 2.7 |
| 1:1 | NMP | 21.8 | 2.3 |
| 3:1 | MEP | 79.7 | 4.2 |
| 3:1 | NMP | 58.0 | 4.2 |
| 5:1 | MEP | 258.0 | 14.9 |
| 5:1 | NMP | 74.6 | 9.2 |

Based on test results in Table II, it is concluded that N-(β-mercaptoethyl)-2-pyrrolidone would be more effective than N-methyl-2-pyrrolidone as solvent in the extractive distillation of feeds containing ether(s), aliphatic hydrocarbon(s) and alcohol(s), especially at a solvent: feed ratio of about 5:1 or higher.

EXAMPLE III

This example demonstrates that mixtures of N-methyl-2-pyrrolidone (NMP) and either sulfolane or tetraethylene glycol (TEG) were more effective than NMP alone or TEG alone in the extractive distillation of an ether/hydrocarbon/alcohol feed.

Tests were carried out substantially in accordance with the procedure described in Example I, except that NMP, a mixture of 50 weight-% NMP and 50 weight-% sulfolane, and a mixture of 25 weight-% NMP and 75 weight-% TEG were used as solvents. Test results are summarized in Table III. The feed had the same composition as the one used in Example I.

TABLE III

| Solvent:Feed Ratio | Added Solvent | Relative Volatility $R^1$ | Relative Volatility $R^2$ |
| --- | --- | --- | --- |
| 0 | None | 14.6 | 0.4 |
| 1:1 | NMP | 21.8 | 2.3 |
| 1:1 | Sulfolane | 22.0 | 1.3 |
| 1:1 | NMP + Sulfolane | 20.9 | 1.6 |
| 1:1 | TEG | 24.9 | 2.6 |
| 1:1 | NMP + TEG | 47.9 | 3.1 |
| 3:1 | NMP | 58.7 | 4.2 |
| 3:1 | Sulfolane | 22.7 | 1.7 |
| 3:1 | NMP + Sulfolane | 63.3 | 3.3 |
| 3:1 | TEG | 57.3 | 5.5 |
| 3:1 | NMP + TEG | 66.2 | 3.9 |
| 5:1 | NMP | 74.6 | 9.2 |
| 5:1 | Sulfolane | 35.6 | 4.9 |
| 5:1 | NMP + Sulfolane | 101.7 | 6.1 |
| 5:1 | TEG | — | — |
| 5:1 | NMP + TEG | 105.6 | 4.8 |

Based on the $R^1$ results in Table III, it is concluded that mixtures of N-methyl-2-pyrrolidone and sulfolane and mixtures of N-methyl-2-pyrrolidone and tetraethylene glycol will generally accomplish a more effective hydrocarbon-alcohol separation than the single solvents, in particular at commercially more feasible solvent: feed ratios of about 3:1 and higher.

Reasonable variations, modifications and adaptations for various usages and conditions can be made within the scope of the disclosure and the appended claims, without departing from the scope of this invention.

That which is claimed is:

1. A process for recovering ethers from mixtures of ethers, aliphatic hydrocarbons and alcohols comprising extractive distillation of a feed consisting essentially of (a) at least one ether containing 4–8 carbon atoms per molecule, (b) at least one aliphatic hydrocarbon selected from the group consisting of alkanes and alkenes, said alkanes containing 3–7 carbon atoms per molecule and said alkenes containing 3–7 carbon atoms per molecule and (c) at least one saturated aliphatic alcohol containing 1–5 carbon atoms and one OH group per molecule, said extractive distillation employing a solvent consisting essentially of at least one sulfolane compound containing 4–8 carbon atoms per molecule and having the general formula of

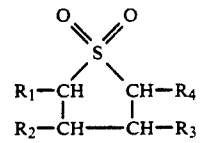

wherein $R_1$, $R_2$, $R_3$, and $R_4$ are independently selected from the group consisting of hydrogen and methyl;
wherein said extractive distillation produces (i) an overhead product which contains a larger volume percentage of said at least one ether than said feed, a larger volume percentage of said at least one aliphatic hydrocarbon than said feed and a smaller volume percentage of said at least one saturated aliphatic alcohol than said feed, and (ii) a bottoms product which contains said solvent, a smaller percentage of said at least one ether than said feed, a smaller percentage of said at least one aliphatic hydrocarbon than said feed and a larger percentage of said at least one saturated aliphatic alcohol than said feed; and
wherein said at least one ether is separated and recovered from said overhead product, and said solvent is separated and recovered from said bottoms product.

2. A process in accordance with claim 1, wherein said at least one sulfolane compound is selected from the group consisting of cyclotetramethylene sulfone, 2-methylsulfolane, 3-methylsulfolane, 2,3-dimethylsulfolane, 2,4-dimethylsulfolane and 2,3,4,5-tetramethylsulfolane.

3. A process in accordance with claim 1, wherein said at least one sulfolane compound is cyclotetramethylene sulfone.

4. A process in accordance with claim 1, wherein in said feed the weight ratio of (a) to (b) is in the range of about 0.2:1 to about 4:1 and the weight ratio of (a) to (c) is about 4:1 to about 30:1.

5. A process in accordance with claim 1, wherein said at least one ether is methyl tertiary-butyl ether, said at least one aliphatic hydrocarbon is selected from the group consisting of isobutane and isobutene, and said at least one saturated aliphatic alcohol is methanol.

6. A process in accordance with claim 1, wherein said at least one ether is ethyl tertiary-butyl ether, said at least one aliphatic hydrocarbon is selected from the group consisting of isobutane and isobutene, and said at least one saturated aliphatic alcohol is ethanol.

7. A process in accordance with claim 1, wherein the weight ratio of said at least one solvent to said feed is in the range of about 1:1 to about 40:1.

8. A process in accordance with claim 1, wherein said at least one ether is separated and recovered from said overhead product by distillation.

9. A process for recovering ethers from mixtures of ethers, aliphatic hydrocarbons and alcohols comprising extractive distillation of a feed consisting essentially of (a) at least one ether containing 4–8 carbon atoms per molecule, (b) at least one aliphatic hydrocarbon selected from the group consisting of alkanes and alkenes, said alkanes containing 3–7 carbon atoms per molecule and said alkenes containing 3–7 carbon atoms per molecule and (c) at least one saturated aliphatic alcohol containing 1–5 carbon atoms and one OH group per molecule, said extractive distillation employing a solvent consisting essentially of a mixture of at least one sulfolane compound containing 4–8 carbon atoms per molecule and having the general formula of

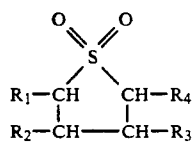

wherein $R_1$, $R_2$, $R_3$, and $R_4$ are independently selected from the group consisting of hydrogen and methyl, and at least one dialkyl sulfone having the formula $R^1-SO_2-R^2$ wherein $R^1$ and $R^2$ are independently selected from the group consisting of alkyl and hydrogen said alkyl containing 1–8 carbon atoms;

wherein said extractive distillation produces (i) an overhead product which contains a larger volume percentage of said at least one ether than said feed, a larger volume percentage of said at least one aliphatic hydrocarbon than said feed and a smaller volume percentage of said at least one saturated aliphatic alcohol than said feed, and (ii) a bottoms product which contains said solvent, a smaller percentage of said at least one ether than said feed, a smaller percentage of said at least one aliphatic hydrocarbon than said feed and a larger percentage of said at least one saturated aliphatic alcohol than said feed; and wherein said at least one ether is separated and recovered from said overhead product, and said solvent is separated and recovered from said bottoms product.

10. A process in accordance with claim 9, wherein said at least one sulfolane compound in said mixture is selected from the group consisting of cyclotetramethylene sulfone, 2-methysulfolane, 3-methylsulfolane, 2,3-dimethylsulfolane, 2,4-dimethylsulfolane and 2,3,4,5-tetramethylsulfolane.

11. A process in accordance with claim 9, wherein the weight ratio of said at least one sulfolane compound to said at least one dialkyl sulfone in said solvent is in the range of about 0.05:1 to about 20:1.

12. A process in accordance with claim 9, wherein said at least one sulfolane compound is cyclotetramethylene sulfone and said at least one dialkyl sulfone is di(n-propyl) sulfone.

13. A process in accordance with claim 9, wherein in said feed the weight ratio of (a) to (b) is in the range of about 0.2:1 to about 4:1 and the weight ratio of (a) to (c) is about 4:1 to about 30:1.

14. A process in accordance with claim 9, wherein said at least one ether is methyl tertiary-butyl ether, said at least one aliphatic hydrocarbon is selected from the group consisting of isobutane and isobutene, and said at least one saturated aliphatic alcohol is methanol.

15. A process in accordance with claim 9, wherein said at least one ether is ethyl tertiary-butyl ether, said at least one aliphatic hydrocarbon is selected from the group consisting of isobutane and isobutene, and said at least one saturated aliphatic alcohol is ethanol.

16. A process in accordance with claim 9, wherein the weight ratio of said at least one solvent to said feed is in the range of about 1:1 to about 40:1.

17. A process in accordance with claim 9, wherein said at least one ether is separated and recovered from said overhead product by distillation.

18. A process for recovering ethers from mixtures of ethers, aliphatic hydrocarbons and alcohols comprising extractive distillation of a feed consisting essentially of (a) at least one ether containing 4–8 carbon atoms per molecule, (b) at least one aliphatic hydrocarbon selected from the group consisting of alkanes and alkenes, said alkanes containing 3–7 carbon atoms per molecule and said alkenes containing 3–7 carbon atoms per molecule and (c) at least one saturated aliphatic alcohol containing 1–5 carbon atoms and one OH group per molecule, said extractive distillation employing a solvent consisting essentially of a mixture of at least one sulfolane compound containing 4–8 carbon atoms per molecule and having the general formula of

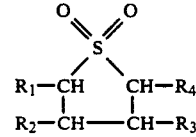

wherein $R_1$, $R_2$, $R_3$, and $R_4$ are independently selected from the group consisting of hydrogen and methyl, and at least one N-alkyl-2-pyrrolidone wherein the alkyl group contains 1–3 carbon atoms;

wherein said extractive distillation produces (i) an overhead product which contains a larger volume percentage of said at least one ether than said feed, a larger volume percentage of said at least one aliphatic hydrocarbon than said feed and a smaller volume percentage of said at least one saturated aliphatic alcohol than said feed, and (ii) a bottoms product which contains said solvent, a smaller percentage of said at least one ether than said feed, a smaller percentage of said at least one aliphatic hydrocarbon than said feed and a larger percentage of said at least one saturated aliphatic alcohol than said feed; and wherein said at least one ether is separated and recovered from said overhead product, and said solvent is separated and recovered from said bottoms product.

19. A process in accordance with claim 18, wherein said at least one sulfolane compound in said mixture is selected from the group consisting of cyclotetramethylene sulfone, 2-methylsulfolane, 3-methylsulfolane, 2,3-dimethylsulfolane, 2,4-dimethylsulfolane and 2,3,4,5,-tetramethylsulfolane.

20. A process in accordance with claim 18, wherein said at least one sulfolane compound is cyclotetramethylene sulfone, and said at least one N-alkyl-2-pyrrolidone is N-methyl-2-pyrrolidone.

21. A process in accordance with claim 18, wherein the weight ratio of said at least one sulfolane compound to said at least one N-alkyl-2-pyrrolidone in said solvent is in the range of about 0.05:1 to about 20:1.

22. A process in accordance with claim 18, wherein in said feed the weight ratio of (a) to (b) is in the range of about 0.2:1 to about 4:1, and the weight ratio of (a) to (c) is about 4:1 to about 30:1.

23. A process in accordance with claim 18, wherein said at least one ether is methyl tertiary-butyl ether, said at least one aliphatic hydrocarbon is selected from the group consisting of isobutane and isobutene, and said at least one saturated aliphatic alcohol is methanol.

24. A process in accordance with claim 18, wherein said at least one ether is ethyl tertiary-butyl ether, said at least one aliphatic hydrocarbon is selected from the group consisting of isobutane and isobutene, and said at least one saturated aliphatic alcohol is ethanol.

25. A process in accordance with claim 18, wherein the weight ratio of said at least one solvent to said feed is in the range of about 1:1 to about 40:1.

26. A process in accordance with claim 18, wherein said at least one ether is separated and recovered from said overhead product by distillation.

27. A process for recovering ethers from mixtures of ethers, aliphatic hydrocarbons and alcohols comprising extractive distillation of a feed consisting essentially of (a) at least one ether containing 4-8 carbon atoms per molecule, (b) at least one aliphatic hydrocarbon selected from the group consisting of alkanes and alkenes, said alkanes containing 3-7 carbon atoms per molecule and said alkenes containing 3-7 carbon atoms per molecule and (c) at least one saturated aliphatic alcohol containing 1-5 carbon atoms and one OH group per molecule, said extractive distillation employing a solvent consisting essentially of at least one dialkyl sulfone having the formula $R^1$—$SO_2$—$R^2$ wherein $R^1$ and $R^2$ are independently selected from the group consisting of alkyl and hydrogen, said alkyl containing 1-8 carbon atoms;

wherein said extractive distillation produces (i) an overhead product which contains a larger volume percentage of said at least one ether than said feed, a larger volume percentage of said at least one aliphatic hydrocarbon than said feed and a smaller volume percentage of said at least one saturated aliphatic alcohol than said feed, and (ii) a bottoms product which contains said solvent, a smaller percentage of said at least one ether than said feed, a smaller percentage of said at least one aliphatic hydrocarbon than said feed and a larger percentage of said at least one saturated aliphatic alcohol than said feed; and wherein said at least one ether is separated and recovered from said overhead product, and said solvent is separated and recovered from said bottoms product.

28. A process in accordance with claim 27, wherein said at least one dialkyl sulfone is di(n-propyl) sulfolane.

29. A process in accordance with claim 27, wherein in said feed the weight ratio of (a) to (b) is in the range of about 0.2:1 to about 4:1, and the weight ratio of (a) to (c) is about 4:1 to about 30:1.

30. A process in accordance with claim 27, wherein said at least one ether is methyl tertiary-butyl ether, said at least one aliphatic hydrocarbon is selected from the group consisting of isobutane and isobutene, and said at least one saturated aliphatic alcohol is methanol.

31. A process in accordance with claim 27, wherein said at least one ether is ethyl tertiary-butyl ether, said at least one aliphatic hydrocarbon is selected from the group consisting of isobutane and isobutene, and said at least one saturated aliphatic alcohol is ethanol.

32. A process in accordance with claim 27, wherein the weight ratio of said at least one solvent to said feed is in the range of about 1:1 to about 40:1.

33. A process in accordance with claim 27, wherein said at least one ether is separated and recovered from said overhead product by distillation.

34. A process for recovering ethers from mixtures of ethers, aliphatic hydrocarbons and alcohols comprising extractive distillation of a feed consisting essentially of (a) at least one ether containing 4-8 carbon atoms per molecule, (b) at least one aliphatic hydrocarbon selected from the group consisting of alkanes and alkenes, said alkanes containing 3-7 carbon atoms per molecule and said alkenes containing 3-7 carbon atoms per molecule and (c) at least one saturated aliphatic alcohol containing 1-5 carbon atoms and one OH group per molecule, said extractive distillation employing a solvent consisting essentially of a mixture of at least one N-(β-mercaptoalkyl)-2-pyrrolidone having the general formula of

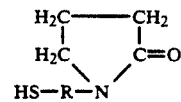

wherein R is a radical selected from the group consisting of —$CH_2$—, —$CH_2$—$CH_2$—, —$CH_2$—$CH_2$—$CH_2$—, —$CH(CH_2)$—$CH_2$—, —$CH_2$—$CH(CH_2)$—, —$CH(CH_3)$—$CH(CH_3)$—, —$C(CH_3)_2$—, $CH(CH_3)$—, —$CH_2$—$CH_2$—$CH_2$—, —$CH_2$—$CH_2$—$CH_2$—$CH_2$— and —$CH_2$—$CH_2$—$CH_2$—$CH_2$—$CH_2$—;

wherein said extractive distillation produces (i) an overhead product which contains a larger volume percentage of said at least one ether than said feed, a larger volume percentage of said at least one aliphatic hydrocarbon than said feed and a smaller volume percentage of said at least one saturated aliphatic alcohol than said feed, and (ii) a bottoms product which contains said solvent, a smaller percentage of said at least one ether than said feed, a smaller percentage of said at least one aliphatic hydrocarbon than said feed and a larger percentage of said at least one saturated aliphatic alcohol than said feed; and wherein said at least one ether is separated and recovered from said overhead product, and said solvent is separated and recovered from said bottoms product.

35. A process in accordance with claim 34, wherein said at least one N-($\beta$-mercaptoalkyl)-2-pyrrolidone is N-($\beta$-mercaptoethyl)-2-pyrrolidone.

36. A process in accordance with claim 34 wherein in said feed the weight ratio of (a) to (b) is in the range of about 0.2:1 to about 4:1, and the weight ratio of (a) to (c) is about 4:1 to about 30:1.

37. A process in accordance with claim 34 wherein said at least one ether is methyl tertiary-butyl ether, said at least one aliphatic hydrocarbon is selected from the group consisting of isobutane and isobutene, and said at least one saturated aliphatic alcohol is methanol.

38. A process in accordance with claim 34, wherein said at least one ether is ethyl tertiary-butyl ether, said at least one aliphatic hydrocarbon is selected from the group consisting of isobutane and isobutene, and said at least one saturated aliphatic alcohol is ethanol.

39. A process in accordance with claim 34, wherein the weight ratio of said at least one solvent to said feed is in the range of about 1:1 to about 40:1.

40. A process in accordance with claim 34, wherein said at least one ether is separated and recovered from said overhead product by distillation.

41. A process for recovering ethers from mixtures of ethers, aliphatic hydrocarbons and alcohols comprising extractive distillation of a feed consisting essentially of (a) at least one ether containing 4–8 carbon atoms per molecule, (b) at least one aliphatic hydrocarbon selected from the group consisting of alkanes and alkenes, said alkanes containing 3–7 carbon atoms per molecule and said alkenes containing 3–7 carbon atoms per molecule and (c) at least one saturated aliphatic alcohol containing 1–5 carbon atoms and one OH group per molecule, said extractive distillation employing a solvent consisting essentially of a mixture of at least one N-alkyl-2-pyrrolidone wherein the alkyl group contains 1–3 carbon atoms, and at least one glycol compound having the general chemical formula of HO—[CHR$^1$—CHR$^2$—O]$_n$—CHR$^1$—CHR$^2$—OH, wherein n can be 0, 1, 2, 3, or 4 and R$^1$ and R$^2$ can be independently selected from the group consisting of hydrogen and methyl;

wherein said extractive distillation produces (i) an overhead product which contains a larger volume percentage of said at least one ether than said feed, a larger volume percentage of said at least one aliphatic hydrocarbon than said feed and a smaller volume percentage of said at least one saturated aliphatic alcohol than said feed, and (ii) a bottoms product which contains said solvent, a smaller percentage of said at least one ether than said feed, a smaller percentage of said at least one aliphatic hydrocarbon than said feed and a larger percentage of said at least one saturated aliphatic alcohol than said feed;

and wherein said at least one ether is separated and recovered from said overhead product, and said solvent is separated and recovered from said bottoms product.

42. A process in accordance with claim 41, wherein said at least one N-alkyl-2-pyrrolidone is N-methyl-2-pyrrolidone, and said at least one glycol compound is selected from the group consisting of ethylene glycol, diethylene glycol, triethylene glycol, tetraethylene glycol and pentaethylene glycol.

43. A process in accordance with claim 42, wherein said at least one glycol compound is tetraethylene glycol.

44. A process in accordance with claim 42, wherein the weight ratio of said at least one N-alkyl-2-pyrrolidone to said at least one glycol compound in said solvent is in the range of about 0.05:1 to about 20:1.

45. A process in accordance with claim 41, wherein in said feed the weight ratio of (a) to (b) is in the range of about 0.2:1 to about 4:1, and the weight ratio of (a) to (c) is about 4:1 to about 30:1.

46. A process in accordance with claim 41, wherein said at least one ether is methyl tertiary-butyl ether, said at least one aliphatic hydrocarbon is selected from the group consisting of isobutane and isobutene, and said at least one saturated aliphatic alcohol is methanol.

47. A process in accordance with claim 41, wherein said at least one ether is ethyl tertiary-butyl ether, said at least one aliphatic hydrocarbon is selected from the group consisting of isobutane and isobutene, and said at least one saturated aliphatic alcohol is ethanol.

48. A process in accordance with claim 41 wherein the weight ratio of said at least one solvent to said feed is in the range of about 1:1 to about 40:1.

49. A process in accordance with claim 41, wherein said at least one ether is separated and recovered from said overhead product by distillation.

* * * * *